United States Patent
Orlow et al.

(10) Patent No.: US 9,526,712 B2
(45) Date of Patent: Dec. 27, 2016

(54) METHODS AND AGENTS FOR PREVENTING AND TREATING PLASMA CELL DYSCRASIAS

(71) Applicant: NEW YORK UNIVERSITY, New York, NY (US)

(72) Inventors: Seth J. Orlow, New York, NY (US); Amitabha Mazumder, East Setauket, NY (US); Nicole Doudican, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/769,888

(22) PCT Filed: Feb. 25, 2014

(86) PCT No.: PCT/US2014/018205
§ 371 (c)(1),
(2) Date: Aug. 24, 2015

(87) PCT Pub. No.: WO2014/130992
PCT Pub. Date: Aug. 28, 2014

(65) Prior Publication Data
US 2016/0008307 A1 Jan. 14, 2016

Related U.S. Application Data

(60) Provisional application No. 61/768,689, filed on Feb. 25, 2013.

(51) Int. Cl.
*A61K 31/198* (2006.01)
*A61K 31/69* (2006.01)
*A61K 45/06* (2006.01)
*C07C 323/58* (2006.01)

(52) U.S. Cl.
CPC .............. *A61K 31/198* (2013.01); *A23L 33/17* (2016.08); *A23L 33/175* (2016.08); *A61K 31/69* (2013.01); *A61K 45/06* (2013.01); *C07C 323/58* (2013.01); *A23V 2002/00* (2013.01)

(58) Field of Classification Search
CPC ...... A61K 31/69; A61K 31/198; C07C 323/58
See application file for complete search history.

(56) References Cited

U.S. PATENT DOCUMENTS

| 8,217,084 B2 | 7/2012 | Ott |
| 8,222,299 B2 | 7/2012 | Ott |
| 2009/0036534 A1 | 2/2009 | Shu et al. |

OTHER PUBLICATIONS

Lea et al. Nutrition and Cancer, (2002), 43(1), p. 90-102.*
FDA drug approval of bortezomib Announce (2008).*
Aggarwal BB et al (2004) Suppression of the nuclear factor-kappaB activation pathway by spice-derived phytochemicals: reasoning for seasoning Ann NY Acad Sci 1030:434-441.
Aggarwal BB et al (2006) Molecular targets of dietary agents for prevention and therapy of cancer. Biochemical Pharmacology 71(10):1397-1421.
Borek C (2001) Antioxidant health effects of aged garlic extract J Nutr 131(3s):1010S-1015S.
Butt MS et al (2009) Garlic: nature's protection against physiological threats Crit Rev Food Sci Nutr 49(6):538-551.
Cooper JL et al (2005) Aminotransferase, L-amino acid oxidase and beta-lyase reactions involving L-cysteine S-conjugates found in allium extracts. Relevance to biological activity? Biochemical Pharmacology 69(2):209-220.
Dorai T et al (2004) Role of chemopreventive agents in cancer therapy Cancer Letters 215(2):129-140.
Doudican, NA et al (2012) Sulforaphane synergistically enhances the cytotoxicity of arsenic trioxide in multiple myeloma cells via stress-mediated pathways Oncology Reports 28(5):1851-1858.
Fleischauer AT et al (2000) Garlic consumption and cancer prevention: meta-analyses of colorectal and stomach cancers Am J Clin Nutr 72(4):1047-1052.
Howard EW et al (2007) Garlic-derived S-allylmercaptocysteine is a novel in vivo antimetastatic agent for androgen-independent prostate cancer Clin Cancer Res 13(6):1847-1856.
Ide, N et al (2001) Garlic compounds minimize intracellular oxidative stress and inhibit nuclear factor-kappa b activation J Nutr. 131(3s):1020S-1026S.
Kelloff GJ et al (1994) Chemopreventive drug development: perspectives and progress Cancer Epidemiol Biomarkers Prev 3(1):85-98.
Kelloff GJ et al (1996) New agents for cancer chemoprevention J Cellular Biochem 26S:1-28.
Khanum et al (2004) Anticarcinogenic properties of garlic: a review Crit Rev Food Sci Nutr.44(6):479-488.

(Continued)

Primary Examiner — Yong Chu
(74) Attorney, Agent, or Firm — Klauber & Jackson LLC

(57) ABSTRACT

Screening assays and methods of using same for screening to identify modulator agents or compounds that target endoplasmic reticulum stress related signaling pathways to induce apoptosis are described herein. Pharmaceutical compositions comprising modulator agents or compounds identified by screening assays described herein are also encompassed. Methods for treating a myeloproliferative disorder characterized by monoclonal plasma cell proliferation in a subject using the aforementioned modulator agents or compounds are also envisioned. Modulator agents or compounds thereof for use in treating a myeloproliferative disorder in a subject and use of modulator agents or compounds thereof in the preparation of medicaments for the treatment of a myeloproliferative disorder are also encompassed herein. Exemplary myeloproliferative disorders include: monoclonal gammopathy of undetermined significance (MGUS), smoldering multiple myeloma (SMM), and multiple myeloma (MM).

18 Claims, 6 Drawing Sheets

(56) References Cited

OTHER PUBLICATIONS

Korde N et al (2011) Monoclonal gammopathy of undetermined significance (MGUS) and smoldering multiple myeloma (SMM): novel biological insights and development of early treatment strategies Blood 117(21):5573-5581.
Lamm DL et al (2001) Enhanced immunocompetence by garlic: role in bladder cancer and other malignancies J Nutr. 131(3s):1067S-1070S.
Landgren O et al (2006) Risk of monoclonal gammopathy of undetermined significance (MGUS) and subsequent multiple myeloma among African American and white veterans in the United States Blood 107(3):904-906.
Lau BHS (2001) Suppression of LDL oxidation by garlic J Nutr 131(3s):9855-9885.
Lawson LD et al (2005) Composition, stability, and bioavailability of garlic products used in a clinical trial J Agric Food Chem 53(16):6254-6261.
Liang D et al (2011) S-allylmercaptocysteine effectively inhibits the proliferation of colorectal cancer cells under in vitro and in vivo conditions Cancer Lett. 310(1):69-76.
Melino S et al (2011) Allyl sulfur compounds and cellular detoxification system: effects and perspectives in cancer therapy Amino Acids 41(1):103-112.
Milner JA (2006) Preclinical perspectives on garlic and cancer J Nutr 1363 Suppl:827S-831S.
Miron T et al (2003) Inhibition of tumor growth by a novel approach: in situ allicin generation using targeted alliinase delivery Mol Cancer Ther 2(12):1295-301.
Nishikori M (2005) Classical and Alternative NF-κB Activation Pathways and Their Roles in Lymphoid Malignancies Journ of Clin & Exper Hematopathology 45(1):15-24.
Pinto JT et al (1997) Effects of garlic thioallyl derivatives on growth, glutathione concentration, and polyamine formation of human prostate carcinoma cells in culture Am J Clin Nutr. 66(2):398-405.
Pinto JT et al (2006) Redox-sensitive proteins are potential targets of garlic-derived mercaptocysteine derivatives J Nutr. 136(3 Suppl):835S-841S.
Powolny AA et al (2008) Multitargeted prevention and therapy of cancer by diallyl trisulfide and related Allium vegetable-derived organosulfur compounds Cancer Letters 269(2):305-314.
Prasad HK et al (2007) Smoldering multiple myeloma N Engl J Med. 357(10):1048-1050.
Riggs DR et al (1997) Allium sativum (garlic) treatment for murine transitional cell carcinoma Cancer 79(10):1987-1994.
Ross SA et al (2006) Allyl sulfur compounds from garlic modulate aberrant crypt formation J Nutr 136(3 Suppl):852S-854S.
Shirin H et al (2001) Antiproliferative effects of S-allylmercaptocysteine on colon cancer cells when tested alone or in combination with sulindac sulfide Cancer Res 61(2):725-731.
Shukla Y et al (2007) Cancer chemoprevention with garlic and its constituents Cancer Lett 247(2):167-181.
Sumiyoshi H et al (1990) Chemoprevention of 1,2-dimethylhydrazine-induced colon cancer in mice by naturally occurring organosulfur compounds Cancer Res 50(16):5084-5087.
Sumiyoshi H (1997) New pharmacological activities of garlic and its constituents Nihon Yakurigaku zasshi 110(Supp 1):93P-97P—Abstract Only.
Sundaram SG et al (1996) Diallyl disulfide induces apoptosis of human colon tumor cells Carcinogenesis 17(4):669-673.
Wang Q et al (2012) Risk factors for multiple myeloma: a hospital-based case-control study in Northwest China Cancer Epidemiology 36(5):439-444.
FDA Drug Velcade bortezomib approved for initital treatment of patients with multiple myeloma Jun. 23, 2008.

* cited by examiner

1. Ladder
2. Positive control (10 ng/ML tunicamycin)
3. 0.5 uM SAC (KMS11 cells)
4. 0.5 uM SAC (ARP1 cells)
5. No treatment

METHODS AND AGENTS FOR PREVENTING AND TREATING PLASMA CELL DYSCRASIAS

CROSS REFERENCE TO RELATED APPLICATIONS

The present application is a National Stage Application which claims priority under 35 USC §120 from co-pending PCT Application No. PCT/US2014/018205, filed Feb. 25, 2014, which in turn claims priority under 35 USC §119(e) from U.S. Provisional Application Ser. No. 61/768,689, filed Feb. 25, 2013, each of which applications is herein specifically incorporated by reference in its entirety.

GOVERNMENTAL SUPPORT

The research leading to the present invention was supported, at least in part, by National Institutes of Health Grant No. AR041880. Accordingly, the Government has certain rights in the invention.

FIELD OF THE INVENTION

Methods for treating myeloproliferative disorders, such as monoclonal gammopathy of undetermined significance (MGUS), smoldering myeloma (SMM), and multiple myeloma (MM) are described herein. In a particular embodiment, such methods comprise administering S-allylcysteine (SAC), compounds comprising SAC, or compositions thereof to a patient afflicted with MGUS, SMM, or MM. Use of SAC, compounds comprising SAC, or compositions thereof for treating MGUS, SMM, or MM and in the manufacture of a medicament for treating a myeloproliferative disorder, such as MGUS, SMM, or MM, are also encompassed herein.

BACKGROUND OF THE INVENTION

The citation of references herein shall not be construed as an admission that such is prior art to the present invention.

Monoclonal gammopathy of undetermined significance (MGUS) and smoldering multiple myeloma (SMM) are asymptomatic myeloproliferative disorders characterized by monoclonal plasma cell proliferation. It is estimated that approximately 5% of the population above the age of 50 is affected by plasma cell dyscrasias [Kyle et al. *N Engl J Med* 354, 1362-1369, 2006]. Both conditions consistently precede multiple myeloma (MM), an incurable malignancy of terminally differentiated B cells, with recent studies demonstrating that these conditions represent one disease on a disease spectrum [Landgren. *Hematology Am Soc Hematol Educ Program* 2010, 295-302]. For patients with MGUS or SMM, the lifetime risk of progression to MM is estimated to be 15-59% [Perez-Persona et al. *Blood* 110, 2586-2592, 2007]. Consequently, MGUS and SMM patients require indefinite follow-up. Currently there is no accepted prevention or treatment strategy available for either condition—patients simply undergo continuous monitoring of plasma markers [Kumar. *Cancer Treat Rev* 36 Suppl 2, S3-11].

Once MM develops, patients typically receive the proteasome inhibitor bortezomib (BTZ) as first line treatment. BTZ has demonstrated remarkable response rates in both relapsed and newly diagnosed MM. By virtue of inhibiting the proteasome, BTZ causes accumulation of misfolded proteins in the endoplasmic reticulum (ER) and activation of the unfolded protein response (UPR), which culminates in induction of caspase 12-mediated apoptosis [Chari et al. *Biologics* 4, 273-287, 2010]. An expansive, well developed rough ER highly specialized for the constant synthesis and secretion of large amounts of protein, namely immunoglobulin (Ig), is a defining characteristic of plasma cells. The innate biology of this class of cells is believed to account for the exquisite sensitivity of plasma cell disorders to agents like BTZ which target ER stress related signaling pathways to induce apoptosis.

Given the clinically validated importance of targeting ER stress pathways in the treatment of MM and the biological similarities that exist between SMM and MM [Shah et al. *Leukemia* 23, 1964-1979, 2009], BTZ is also predicted to be effective in the management of MGUS and/or SMM. However, BTZ carries the potential for serious side effects; for example, more than 30% of the patients receiving BTZ treatment develop painful peripheral neuropathy [Cavaletti. *Lancet Oncol* 12, 120-121]. In fact, Takeda Pharmaceuticals recently received FDA approval for administration of BTZ by subcutaneous injection in an effort to reduce the number of patients experiencing severe nerve damage. It is expected that this will become the preferred route of administration. This route of administration, however, along with the potential for harmful side effects, precludes BTZ from being used in the treatment of MGUS/SMM.

SUMMARY OF THE INVENTION

In a first aspect, a method for treating and/or preventing a myeloproliferative disorder characterized by monoclonal plasma cell proliferation in a subject is presented, the method comprising administering a therapeutically effective amount of S-allylcysteine (SAC), a compound comprising SAC, or a composition thereof to a patient afflicted with such a disorder so as to target cells involved in these disorders for cell killing via ER stress mediated pathways. In so doing, the method effectively reduces the number of proliferating monoclonal plasma cells in the subject, thereby treating the subject.

In a second aspect, a method for treating and/or preventing a myeloproliferative disorder characterized by monoclonal plasma cell proliferation in a subject is presented, wherein the myeloproliferative disorder is an asymptomatic myeloproliferative disorder or a symptomatic myeloproliferative disorder, the method comprising administering a therapeutically effective amount of S-allylcysteine (SAC), a compound comprising SAC, or a composition thereof to a patient afflicted with such a disorder so as to target cells involved in these disorders for cell killing via ER stress mediated pathways. In a particular aspect, the asymptomatic myeloproliferative disorder is monoclonal gammopathy of undetermined significance (MGUS) or smoldering multiple myeloma (SMM). In another particular aspect, the symptomatic myeloproliferative disorder is multiple myeloma (MM). In a particular embodiment thereof, the subject has treatment resistant or refractive MM. Such embodiments may further comprise a chemotherapeutic agent, such as, for example, bortezomib (BTZ). BTZ may be administered before, concomitantly, or after SAC or a compound or composition thereof at the discretion of a skilled practitioner. In yet another embodiment, the subject is in remission following successful treatment for MM and methods described herein are implemented to slow or prevent relapse in the patient. Under such circumstances, the methods are implemented for preventive or prophylactic purposes.

In a particular embodiment, the compound or composition consists essentially of SAC or consists of SAC.

In another particular embodiment, the subject is a mammal. In a more particular embodiment, the subject is a human.

In another aspect, a method for treating and/or preventing a myeloproliferative disorder characterized by monoclonal plasma cell proliferation in a patient or patient population is presented, the method comprising providing a patient afflicted with an asymptomatic myeloproliferative disorder or providing a patient population comprising patients afflicted with an asymptomatic myeloproliferative disorder and administering a therapeutically effective amount of S-allylcysteine (SAC), a compound comprising SAC, or a composition thereof to the patient or each one of the patients afflicted with the asymptomatic myeloproliferative disorder so as to target cells involved in this disorder for cell killing via ER stress mediated pathways. In a particular embodiment thereof, the patient or patient population has either MGUS or SMM. In a further embodiment thereof, the patient is a mammal (e.g., a human) or the patient population comprises mammals (e.g., humans). In a particular embodiment, the compound or composition consists essentially of SAC or consists of SAC.

In another aspect, a method for treating and/or preventing a myeloproliferative disorder characterized by monoclonal plasma cell proliferation in a patient or patient population is presented, the method comprising selecting the patient afflicted with a symptomatic myeloproliferative disorder or patient population comprising patients afflicted with a symptomatic myeloproliferative disorder and administering a therapeutically effective amount of S-allylcysteine (SAC), a compound comprising SAC, or a composition thereof to the patient or each one of the patients afflicted with the symptomatic myeloproliferative disorder so as to target cells involved in this disorder for cell killing via ER stress mediated pathways. In a particular embodiment thereof, the patient population has MM. In a particular embodiment thereof, the subject has treatment resistant or refractive MM. Such embodiments may further comprise a chemotherapeutic agent, such as, for example, bortezomib (BTZ). BTZ may be administered before, concomitantly, or after SAC or a compound or composition thereof at the discretion of a skilled practitioner. In yet another embodiment, the subject is in remission following successful treatment for MM and methods described herein are implemented to slow or prevent relapse in the patient. Under such circumstances, methods are implemented for preventive or prophylactic purposes. In a further embodiment thereof, the patient population comprises mammals (e.g., humans). In a particular embodiment, the compound or composition consists essentially of SAC or consists of SAC.

As described herein, the therapeutically effective amount of S-allylcysteine (SAC), a compound comprising SAC, or a composition thereof may be administered via a nutraceutical, a dietary supplement, or a drug. In a particular embodiment, the therapeutically effective amount of S-allylcysteine (SAC) is administered orally. In a more particular embodiment, the therapeutically effective amount of S-allylcysteine (SAC) is administered via AGE tablets. A suitable therapeutic regimen of AGE tablets comprises about 500-2,500 mg of AGE administered per day. In a particular embodiment thereof, three 500 mg AGE tablets are administered per day.

Efficacy of the preventative and/or therapeutic methods described herein can be assessed by assaying a number of parameters, including: measuring the free light-chain ratio (rFLC) and the difference between clonal and nonclonal light-chain (dFLC) and involved free light-chain (iFLC), wherein a reduction in any of these parameters is a positive indicator of efficacy. A decrease in urinary deoxypyridinoline (uDPYD), a marker of bone resorption is also an indicator of efficacy, as is a decrease in serum creatinine levels.

In another aspect, S-allylcysteine (SAC) or a compound or composition thereof is presented for use in the treatment of a myeloproliferative disorder in a subject, wherein the SAC or the compound or composition thereof is administered in a therapeutically effective amount to the subject. The myeloproliferative disorder may be an asymptomatic myeloproliferative disorder or a symptomatic myeloproliferative disorder. In a particular embodiment, the asymptomatic myeloproliferative disorder is MGUS or SMM. In another embodiment, the symptomatic myeloproliferative disorder is MM. In a more particular embodiment, the symptomatic myeloproliferative disorder is treatment resistant MM. Under such circumstances, the aforementioned use may be supplemented with use of chemotherapeutic agent, such as, for example, bortezomib (BTZ). Use of BTZ may entail administering before, concomitantly, or after SAC or a compound or composition thereof at the discretion of a skilled practitioner. In another embodiment, the aforementioned use is envisioned for treating a subject in remission following successful treatment of MM, in which case, the use of SAC or a compound or composition thereof is directed to preventive or prophylactic treatment of such patients so as to delay or prevent relapse to MM. As described herein, subjects and patients may be mammals, and more particularly, may be humans. In a more particular embodiment, the SAC or compound or composition thereof used consists essentially of SAC or consists of SAC.

The therapeutically effective amount of S-allylcysteine (SAC) or the compound or composition thereof is administrable via a nutraceutical, a dietary supplement, or a drug. It may, moreover, be used in an oral formulation. AGE tablets are set forth as exemplary tablets for oral administration. An exemplary dosing regimen calls for use of about 500-2,500 mg of AGE per day. In a particular embodiment thereof, a dosing regimen comprises use of a total of three 500 mg AGE tablets per day. As described herein, efficacy may be determined by measuring clinical indicators of disease comprising free light-chain ratio (rFLC), a differential between clonal and nonclonal light-chain (dFLC), involved free light-chain (iFLC), urinary deoxypyridinoline (uDPYD), and/or serum creatinine levels. In a particular embodiment, a decrease in any one of these clinical indicators of disease is a positive indicator of efficacy.

In another aspect, use of S-allylcysteine (SAC) or a compound or composition thereof for the manufacture of a medicament for treating a myeloproliferative disorder in a subject is envisioned, wherein the medicament is prepared to be administered in a dosage regime whereby SAC or the compound or composition thereof is delivered in a therapeutically effective amount to the subject. The myeloproliferative disorder may be an asymptomatic myeloproliferative disorder (e.g., MGUS or SMM) or a symptomatic myeloproliferative disorder (e.g., MM). In a particular embodiment thereof, the medicament is prepared to be administered to a subject with treatment resistant MM. This embodiment may further comprise a medicament comprising a chemotherapeutic agent, such as, for example, bortezomib (BTZ), which may be administered in conjunction with a medicament comprising SAC or a compound or composition thereof. The medicament comprising BTZ may be administered before, concomitantly, or after a medicament comprising SAC or a compound or composition thereof at the discretion of a skilled practitioner. In another embodiment, the medicament is prepared to be administered to a subject in remission following successful treatment for MM. In accordance with such an implementation, the medicament is administered for preventive or prophylactic purposes so as to delay or prevent relapse to MM. In a particular embodiment, the subject is a mammal. In a more particular embodiment, the mammal is a human. In an even more particular embodiment, the medicament consists essentially of SAC or consists of SAC.

The medicament may be prepared to be administered in the form of a nutraceutical, a dietary supplement, or a drug. In a particular embodiment thereof, the medicament is prepared to be administered orally. In a more particular embodiment, the medicament comprises AGE tablets, which are administrable in a dosing regimen of about 500-2,500 mg of AGE administered per day. In a still more particular embodiment, a total of three 500 mg AGE tablets are administered per day. Efficacy of the medicament may be determined by measuring clinical indicators of disease comprising free light-chain ratio (rFLC), a differential between clonal and nonclonal light-chain (dFLC), involved free light-chain (iFLC), urinary deoxypyridinoline (uDPYD), and/or serum creatinine levels, wherein a decrease in any one of the clinical indicators of disease is a positive indicator of efficacy.

Other objects and advantages will become apparent to those skilled in the art from a review of the ensuing detailed description, which proceeds with reference to the following illustrative drawings, and the attendant claims.

DETAILED DESCRIPTION

Figure 1:
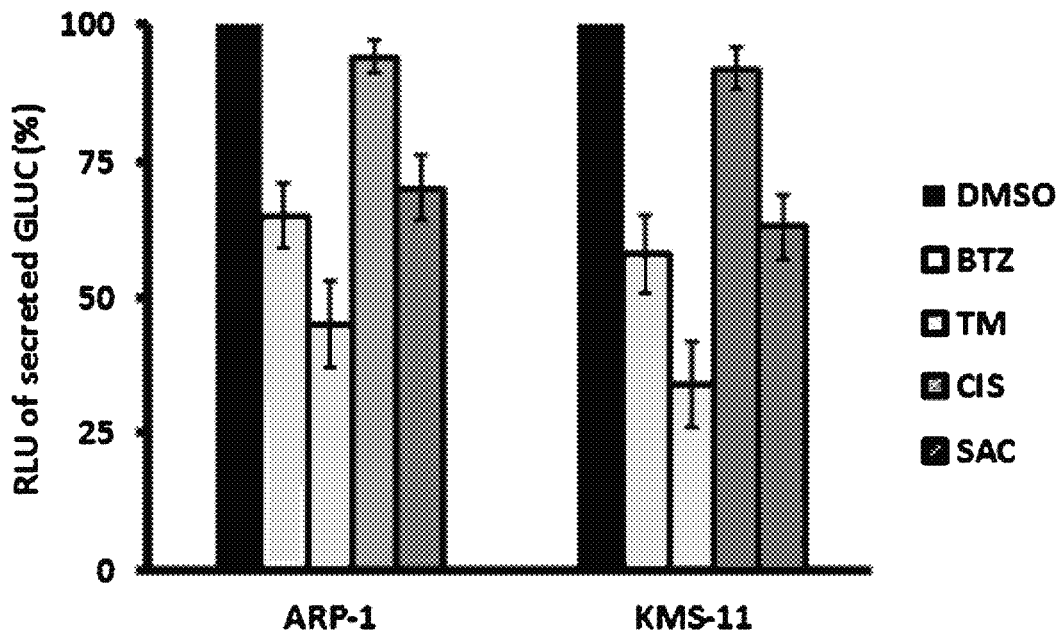
FIG. 1 shows that SAC (5 μM) inhibits Gluc secretion as effectively as 5 μM BTZ. 10 ng/Ml TM and 5 μM CIS serve as positive and negative controls, respectively. Gluc secretion is expressed as % RLU relative to DMSO control. Cells were treated for 24 hours.

In an effort to identify an agent appropriate for prolonged use in patients afflicted with MGUS or SMM, the present inventors sought to identify natural products that, like BTZ, target ER stress. These agents have the potential to be clinically useful not only as therapeutic agents in the treatment of MM, but also as chemopreventative agents to inhibit progression of MGUS or SMM to MM. Using a screen specifically designed to identify agents that disrupt protein secretion, the present inventors identified 5-allyl cysteine (SAC), an organosulfur compound found naturally in garlic, as a potent disruptor of myeloma proteastasis and cellular proliferation. Therefore, based upon their preclinical studies, the present inventors propose administration of aged garlic extract (AGE), for example, to patients with MGUS, SMM, or frank myeloma, alone or in combination with other agents, to prevent progression and/or treat the disease.

Further to the above, it is also noteworthy that while chemotherapy is the preferred initial treatment for symptomatic MM, the disease is highly resistant to chemotherapeutic agents and most patients who initially respond to such treatment eventually relapse. Accordingly, MM patients who have been treated successfully and are in remission may benefit from preventative/prophylactic treatment with SAC or compounds or compositions comprising SAC to prevent a relapse and MM patients who have relapsed due to loss of sensitivity to other chemotherapeutic agents may benefit from treatment with SAC or compounds or compositions comprising SAC, either administered alone or in conjunction with chemotherapeutic agents such as, for example, BTZ.

Symptomatic and Asymptomatic Myeloproliferative Disorders

MM is a progressive neoplastic disease characterized by a malignant neoplasm of plasma cells in the bone marrow associated with an overproduction of monoclonal protein. MM can cause anemia, severe bone pain, and in some cases pathological fracture, increased risk of infection, hypercalcaemia and renal failure (Kyle et al. N Engl J Med 2004; 351:1860-1873).

In contrast, MGUS is an asymptomatic plasma cell dyscrasia associated with an overproduction of plasma cell generated monoclonal protein, but is otherwise asymptomatic. Greater than 3% of the general caucasian population over 50 years old has MGUS and the condition is associated with an average multiple myeloma progression risk of 1% per year (Kyle et al. N Engl J Med 2006; 354:1362-1369). While the diagnosis of MGUS requires the absence of anemia, hypercalcemia, renal failure, and lytic bone lesions related to the plasma cell proliferative disorder, the mere presence of one or more of these features in conjunction with an M protein does not automatically indicate MM or related malignancy, since these abnormalities may be due to unrelated coexisting diseases. As an example, patients with MGUS may have anemia related to nutritional deficiency; renal failure related to coexisting diabetes or hypertension; hypercalcemia due to hyperparathyroidism; or lytic bone lesions from metastatic carcinoma. Only patients in whom these clinical findings of end organ damage are felt to be clearly related to the plasma cell disorder are considered to have MM. This information is also pertinent to a SMM diagnosis.

Smoldering multiple myeloma (SMM) is another asymptomatic plasma cell dyscrasia, but is associated with a higher risk of progression to symptomatic MM (10% per year in the first 5 years) as compared with MGUS (Landgren et al. Blood 2006; 107:904-906). SMM exhibits all of the diagnostic criteria of MM, absent lytic bone disease anemia, renal failure, or hypercalcemia (CRAB symptoms). See, for example, Lopez-Corral at al. (Haematologica 97(9):1439-1443, 2012).

TABLE 1

Differential Diagnosis for MGUS, SMM, and MM

| Feature | MGUS | SMM | MM |
| --- | --- | --- | --- |
| Bone marrow clonal plasma cells (BMPC), % | <10 and | ≥10 and/or | ≥10 and/or |
| Serum monoclonal protein, g/L | <3 | ≥3 | ≥3 |
| Clincal manifestation | Absent | Absent | Present* |

*Clinical features may include increased serum calcium concentrations, renal failure, anemia, skeletal involvement (lytic lesions), recurrent bacterial infections, hyperviscosity and/or extramedullary plasmacytomas. See Bladé et al. (J Clin Oncol 28: 680-697, 2009).

Additional details relating to definitions of monoclonal gammopathies are presented in Korde et al. Blood 2011, 117:5573-5581, the entire content of which is incorporated herein by reference.

As understood in the art and indicated herein above, there is no currently accepted prevention or treatment strategy available for SMM or MGUS—patients simply undergo continuous monitoring of plasma markers [Kumar. *Cancer Treat Rev* 36 Suppl 2, S3-11]. Indeed, regular surveillance is the standard for management of multiple myeloma precursor disease at present (Korde et al. Blood 2011, 117:5573-5581). There is, however, interest in treating asymptomatic MGUS/SMM with agents effective against MM, a frank malignancy. The application of this plan is complicated by the fact that drugs used to treat MM, like bortezomib, carry risks of severe side effects that may outweigh the potential benefits, particularly with long term use. Nevertheless, some clinical trials are being conducted to compare the use of myeloma drugs, such as lenalidomide, with surveillance alone. Although early results suggest this approach may be beneficial, the side effects patients incur in an otherwise asymptomatic condition are limiting and may be unacceptable [Maetos et al. in *American Society for Hematology Annual Meeting* (Orlando, Fla., 2010)].

The approach presented herein, which calls for treating these asymptomatic conditions with orally available, naturally occurring SAC differs from the aforementioned studies in many respects, not the least of which is the fact that it does not carry the same risk of side effects. Indeed, use of a natural agent like SAC in the treatment of SMM would represent a paradigm shift in management of plasma cell dyscrasia and chemoprevention of MM, with the potential to reduce both the incidence and mortality of MM.

Given its anti-proliferative activity in MM cells, SAC may also be a useful therapeutic agent in the treatment of MM. It has the potential to inhibit MM cell growth without the deleterious side effects associated with the current standard of care, bortezomib. As mentioned above, bortezomib treatment is associated with painful peripheral neuropathy. SAC potentially offers an effective treatment option without debilitating side effects. Its use in the clinic to treat MM could represent an improvement in patient care and quality of life.

Screen Design and Execution

A distinguishing characteristic of myeloma plasma cells is the large quantity of paraprotein that they synthesize and secrete, rendering them especially sensitive to the effects of endoplasmic reticulum (ER) stress. Consistent with this notion, the proteasome inhibitor bortezomib disrupts protein equilibrium in the ER by preventing misfolded proteins from being properly degraded. Given the clinically validated importance of targeting ER stress mediated pathways in the treatment of multiple myeloma (MM), the present inventors sought to identify natural products that modulate ER stress mediated pathways. In so doing, the present inventors have identified agents (e.g., SAC) that have strong potential to act as effective therapeutic agents for the treatment of MM. Such agents also have potential for use as chemopreventative agents to inhibit progression of asymptomatic MGUS or SMM to symptomatic MM without the limiting side effects of current targeted therapies like bortezomib.

Using decreased protein processing in the secretory pathway as a measurable hallmark of ER stress, the screen described herein employs the naturally secreted Gaussia luciferase (Gluc) as a reporter that can be easily monitored through extracellular release of luciferase activity in real time. KMS11 and ARP-1 MM cells expressing Gluc were exposed to compounds in a natural products library in order to identify those which potentially induce ER stress as measured by inhibition of Gluc secretion. Both KMS11 and ARP-1 are human MM cells lines routinely used in the literature as in vitro models of MM. See, for example, Paterson et al., Br J Haematol, 2004, 124, 595-603; Pedranzini et al., Cancer Res, 2006, 66, 9714-9721; Stein et al., Clin Cancer Res, 2009, 15, 2808-2817; St-Germain J R. et al., Proc Natl Acad Sci USA, 2009, 106, 20127-20132; Gojo et al., Clin Cancer Res, 2002, 8, 3527-3538; Drucker et al., Carcinogenesis, 2006, 27, 197-204; Weiss et al., Br J Cancer, 2012, 107, 1844-1852; and Wang et al., Clin Cancer Res, 2006, 12, 49-56; the entire content of each of which is incorporated herein by reference. Likewise, the GLUC assay for protein secretion is commercially available (New England Biosystems) and does not necessitate special skills for implementation. For screening, KMS11 and ARP1 cells were seeded in 96-well plates and treated with 5 μM of compounds from the Spectrum library (Microsource Discoveries) for 24 hours. Conditioned medium from each compound treatment was harvested to assay Gluc secretion alongside samples treated with DMSO alone, BTZ and TM as controls. Compounds of interest were considered to be those that inhibit Gluc secretion in both cell lines at least 30% after 24 hours treatment. See, for example, FIG. 1.

From 2000 compounds, the present inventors identified 97 hit compounds. Of these compounds, 62 are human drugs, 31 are natural products, and 4 are traditionally used in veterinary medicine. As detailed herein, SAC was identified as one of the promising hit compounds. An assessment of the compound library revealed that no other compounds having a structure strikingly similar to SAC were present in the library screen. Interestingly, alliin (a cysteine sulfoxide found in garlic) was included in the screen but not found to be effective at inhibiting GLUC secretion.

The growth inhibitory activity of SAC was further characterized by MTT assay. These experiments assess cellular proliferation using the CellTiter 96 AQ Non-Radioactive Cell Proliferation Assay (Promega). This assay determines the number of living cells based upon the bioreduction of MTS tetrazolium compound into a colored formazan product. The quantity of product, as measured by absorbance on a microplate reader at 495 nm, is directly proportional to the number of living cells in culture. All cells were seeded in 96-well plates at a density of 5,000 cells per well. After overnight incubation, cells were treated with SAC at the indicated concentrations. After a 72 hr incubation period, proliferation was assessed. Cellular proliferation was expressed as a percentage with vehicle-treated cells set at 100%. See, for example, FIG. 2.

Figure 3:
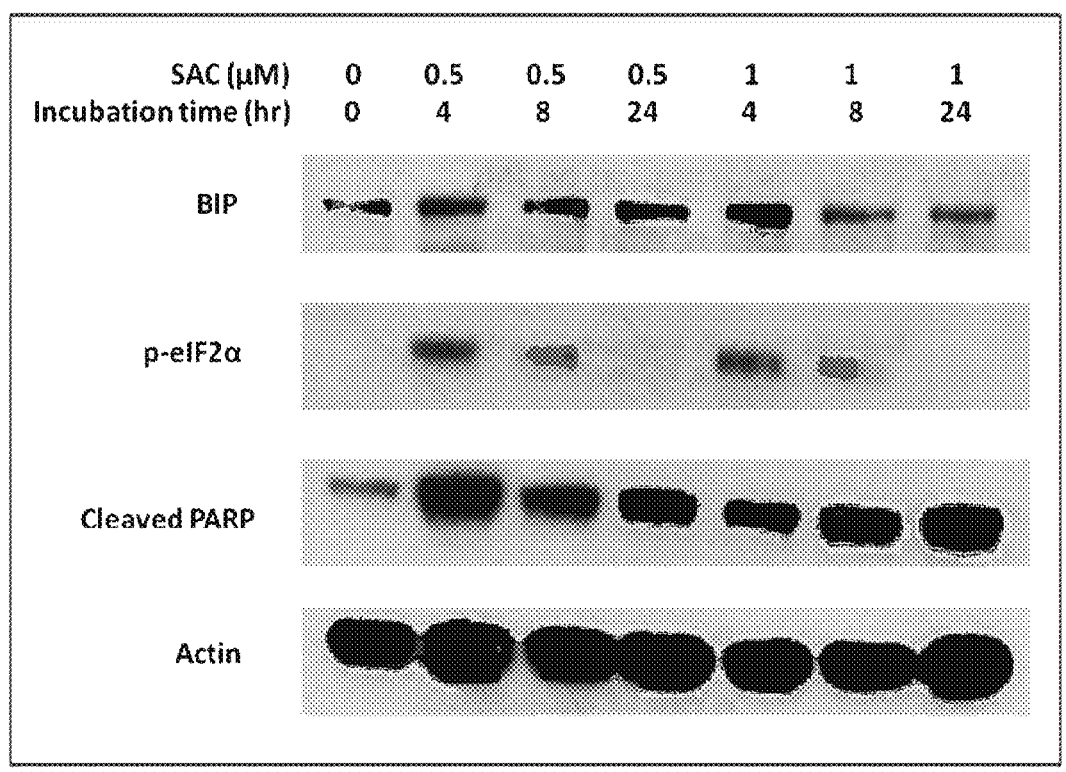
FIG. 3 shows that treatment with SAC induces phosphorylation of eukaryotic initiation factor 2 alpha (eIF2 α), increased immunoglobulin heavy chain binding protein (BIP) expression and cleavage of poly ADP ribose polymerase (PARP) in KMS11 MM cells. Actin serves as a loading control.

In order to investigate the mechanism of SAC mediated ER stress response, the present inventors evaluated key unfolded protein response (UPR) markers including phospho-eIF2α and BIP as well as the apoptotic marker cleaved PARP by standard western blotting techniques. Preliminary data suggests involvement of the UPR in the cellular response to SAC, as indicated by enhanced phosphorylation of eIF2-α, increased BIP expression and cleavage of PARP. See also FIG. 3.

The chemical structure of S-allyl cysteine (SAC) is presented below:

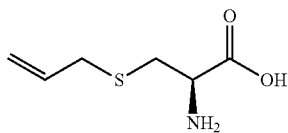

SAC is a non-toxic, water-soluble organosulfur compound that is a minor constituent of fresh garlic. It is a derivative of the amino acid cysteine, wherein an allyl group is appended to the sulfur atom therein. It may also be referred to as DL-S-Allylcysteine; S-Allyl-L-cysteine; (R)-Allylthio-2-aminopropionic acid; L-Deoxyalliin; (L)-3-(Allylsulfenyl)-alanine; Deoxyalliin; Cysteine, S-allyl-L-; and DL-S-Allylcysteine.

The following presents the structures of four water-soluble organosulfur compounds present in garlic and onions, including: SAC; S-propyl cysteine (SPC); S-allyl mercaptocysteine (SAMC); and cysteine (CySH).

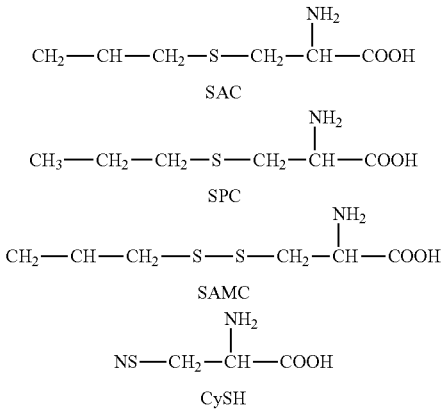

As shown in the structures above, SAC contains a cysteinal radical bonded to an allyl group, with just one sulfur atom in the molecule. In contrast, SAMC contains a cysteinal radical bonded to an allyl-mercapto group, resulting in two sulfur atoms in the molecule, which are bonded together via a disulfide bond. As a consequence, SAMC can participate in disulfide exchange reactions, whereas SAC cannot. In light of its ability to act as an antioxidant, SAMC is generally viewed as having more beneficial medicinal properties than SAC. See, for example, U.S. Pat. No. 8,222,299, the entire content of which is incorporated herein by reference.

The further explore the properties of compounds structurally related to SAC with respect to their potential as agents useful for treating MGUS and SMM and treating and/or preventing MA/I, the present inventors tested the activity of two additional garlic compounds, S-propyl cysteine (SPC) and S-allyl mercaptocysteine (SAMC; also known as SAM), in multiple myeloma cells. As shown in, for example, FIG. 2, SAC inhibits proliferation of multiple myeloma cells. The present inventors determined that the $IC_{50}$ for SAC in ARP1 and KMS11 MM cells is 1.9 μM and 1.5 μM, respectively. By contrast, SPC and SAM appear to have little effect on cellular proliferation in myeloma cells, with the $IC_{50}$ for SPC and SAM being >10 μM in ARP1 and KMS11 cells. See, for example, FIG. 5. Accordingly, despite their structural similarity to SAC, SPC and SAM do not exhibit significant anti-proliferative properties for MM cells and thus, are not good candidates for therapeutic use in subjects afflicted with MGUS, SMM, or MM.

Although not wishing to be bound by theory, the differential activity of SAC versus SPC suggests that the allylic group present in SAC and absent in SPC may contribute to SAC activity, potentially via chelation. The differential activity of SAC versus SAM could be interpreted to suggest that the distance between the allylic (primary chelating) group and a secondary amino/carboxy group may be optimal in SAC, whereas the activity of SAM is impaired as a result of the increased distance between the primary and secondary groups due to the presence of the additional "S" atom in the linker.

Figure 5:
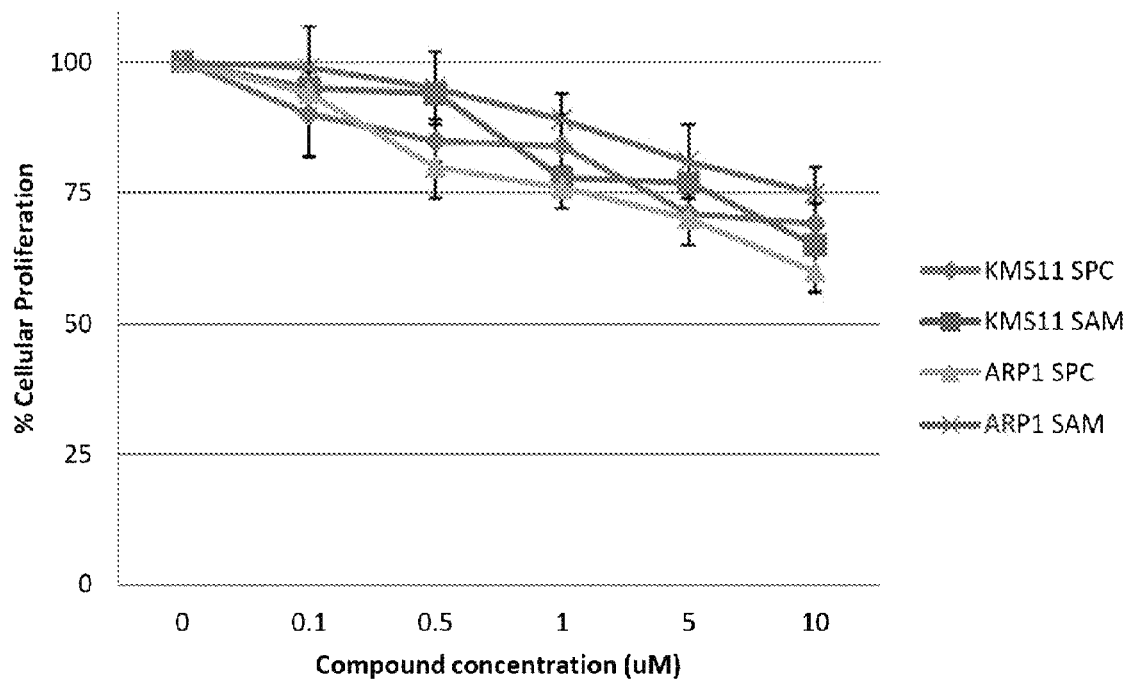
FIG. 5 shows that S-propyl cysteine (SPC) or 5-allyl mercaptocysteine (SAMC; also known as SAM) do not appreciably inhibit cellular proliferation in KMS11 and ARP1 cells. Cellular proliferation was assessed after 72 hour treatment by MTT assay and expressed as a percentage relative to vehicle control.

The cell proliferation assay performed to generate the results presented in FIG. 5, for example, was performed as described elsewhere herein. Briefly, all cells were seeded in 96-well plates at a density of 5000 cells per well. After overnight incubation, cells were treated with a candidate compound at concentrations ranging from 100 nM to 10000 nM. After a 72 hr incubation period, proliferation was assessed using a tetrazolium dye reduction assay (CellTiter 96 AQueous Non-Radioactive Cell Proliferation Assay; Promega, Madison, Wis.). Absorbance was recorded on a microplate reader at 490 nm. Cellular proliferation was expressed as a percentage with vehicle-treated cells set at 100%. Each assay was performed in triplicate with mean values reported.

Figure 6:
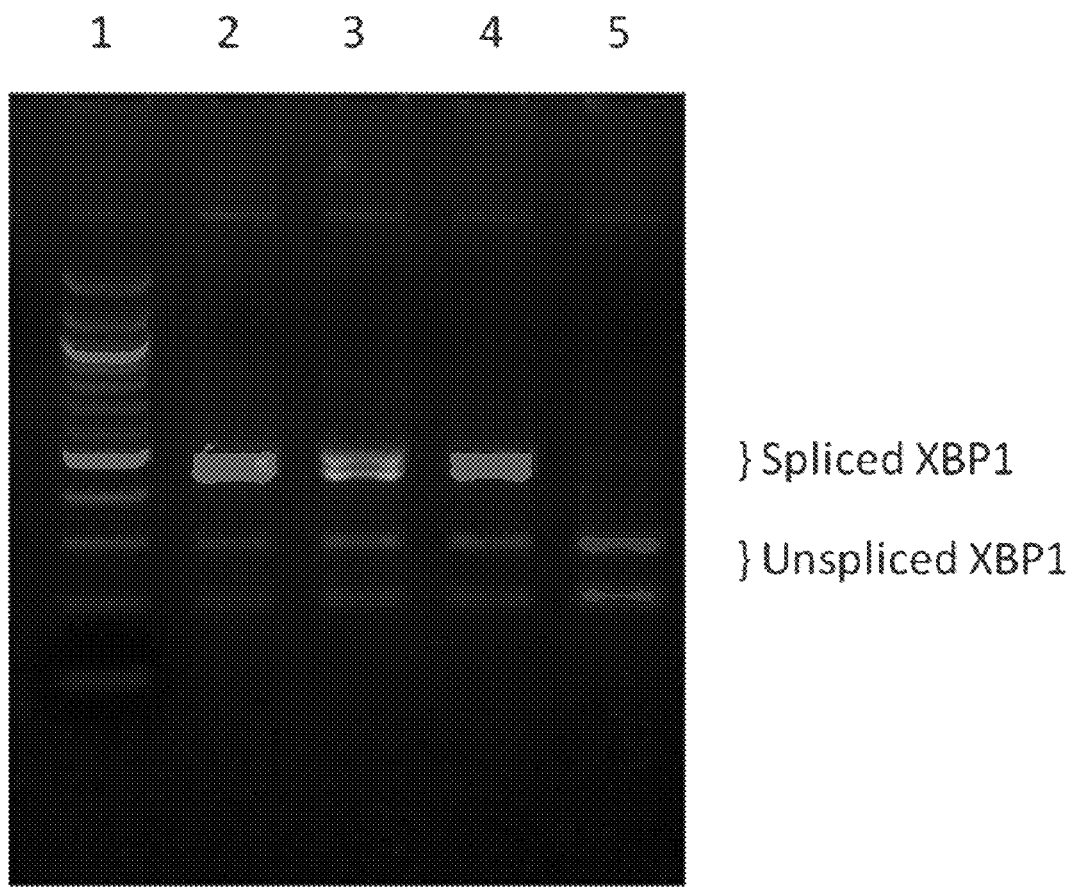
FIG. 6 reveals that SAC induces ER stress as evidenced by XBP1 cleavage in both KMS11 and ARP1 multiple myeloma cells.

The XBP1 cleavage assay used to generate the results presented in FIG. 6 was performed as follows. KMS11 and ARP1 cells were treated with 0.5 uM SAC or 10 ng/ml tunicamycin (TM, positive control) for 24 hours. Total RNA was isolated from lysed cells with the RNeasy Mini kit (Qiagen, Germantown, Md., USA). XBP1 splicing was assessed by semi-quantitative RT-PCR as described previously (Lin, et al. Science, 2007. 318(5852):944-9; Manga et al. Pigment Cell Melanoma Res, 2010. 23(5):627-34; the entire content of each of which is incorporated herein by reference). cDNA was produced from total RNA preps using ImProm-II Reverse Transcription System (Promega). Primers spanning the fragment of XBP1 containing the intron targeted by Irela were used: 5'-TACGGGAGAAAACT-CACGGC-3' and 5'-GGGTCCAACTTGTCCAGAATGC-3'. The thermal PCR cycling conditions are as follows: 95° C. for 5 min, 95° C. for 1 min, 58° C. for 30 s, 72° C. for 30 s, and 72° C. for 5 min with 35 cycles of amplification. In order to properly distinguish the PCR products, samples were digested with Pst1 (New England Biolabs, Ipswich, Mass., USA) that only cuts the unspliced cDNA (Calfon et al. Nature, 2002. 415(6867):92-6). Products were then separated on a 2.0% agarose/1× TAE gel and visualized by ethidium bromide.

Two classes of organosulfur compounds are found in whole garlic cloves: gamma-glutamylcysteines and cysteine sulfoxides. Allylcysteine sulfoxide (alliin) accounts for approximately 80% of the cysteine sulfoxides in garlic. In contrast, SAC is a gamma-glutamylcysteine. Alliin was one of the 2000 compounds screened, but showed no ability to inhibit GLUC secretion.

The chemical structure of alliin is presented below:

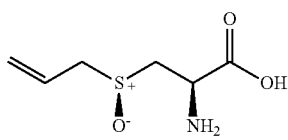

Accordingly, the present findings are surprising in several respects, including recognition of a hitherto unappreciated functional property of SAC, namely the ability to target ER stress mediated pathways. As described herein, the appreciation of this functional property, as described herein, prompted the discovery that SAC can be used to target pathologic cells susceptible to ER stress mediated pathways which are associated with a variety of disorders, including myeloproliferative disorders. The present findings, furthermore, reveal that of organosulfur compounds identified in garlic, the ability to target ER stress mediated pathways is unique to SAC. This point is underscored by the fact that alliicin, which is structurally similar to SAC, did not exhibit an ability to target ER stress mediated pathways.

Figure 4:
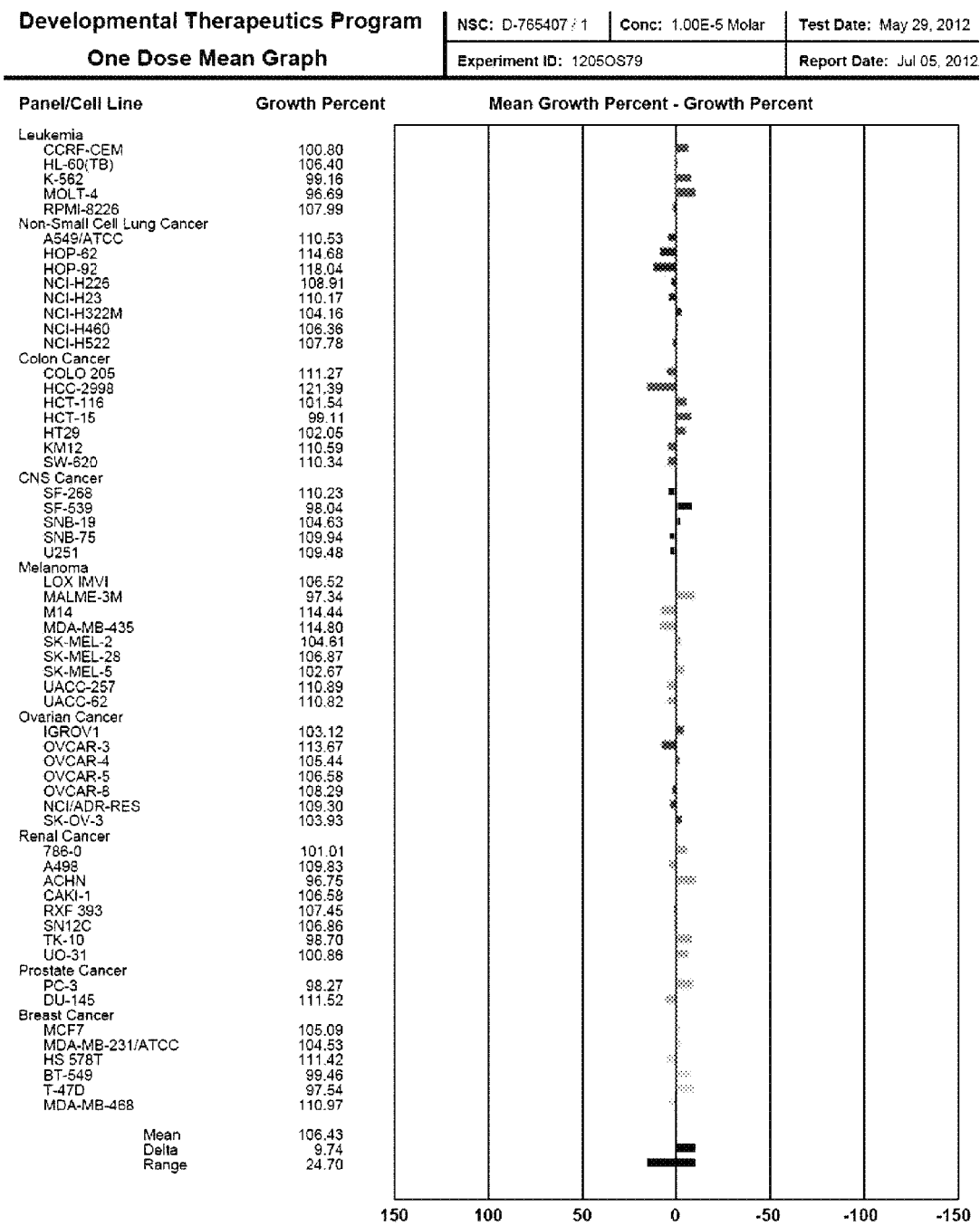
FIG. 4 shows growth inhibitory activity of SAC as assessed for a panel of 60 different cancer cell lines. The mean growth percent across all 60 cell lines is plotted as the center vertical line in the histogram. The mean growth percent for this assessment is 106. Accordingly, any value above 106 is deemed "resistant" with bars plotted to the left of center and any value below 106 is deemed "sensitive" and indicated by bars to the right of center.

Although SAC has been used to treat other types of cancer including colon, lung, breast and liver, the present inventors are unaware of any studies pertaining to its efficacy in MM, MGUS or SMM. One major difference between these types of cancers relates to the fact that those that have been assessed with regard to SAC' s efficacy are solid tumors, whereas MM is a blood cancer. Further to this point, the present inventors submitted SAC for analysis in the Developmental Therapeutics Program at the NCI/NIH. The growth inhibitory activity of SAC was assessed in the NCI 60 cell screen, which is a panel of 60 different cancer cell lines. As shown in FIG. 4, SAC exhibited different growth inhibitory activity across the panel of cell lines dependent upon the etiology of the cell line. These results demonstrate that the anti-cancer activity of SAC with respect to a particular cancer cannot be predicted based on its activity with respect to other cancers. SAC anti-cancer activity must, therefore, be determined empirically for each cancer, due to the lack of predictability of response. Therefore, a compound's ability to act as a therapeutic agent in one cancer, e.g. colon, is not necessarily predictive of its properties with respect to a different cancer, even a related cancer. It is also noteworthy that no MM cell lines are represented in the 60 cell panel. This underscores the fact that, in advance of the present findings, MM cell lines were not thought to be suitable targets for examining SAC anti-cancer activity.

The medicinal properties of garlic are well established. Epidemiological studies have found that increased intake of garlic and/or its active constituents is associated with a reduced risk of colon cancer [Khanum et al. Crit Rev Food Sci Nutr 44:479-488, 2004; Steinmetz et al. Am J Epidemiol 139:1-15, 1994; Fleischauer et al. Am J Clin Nutr 72:1047-1052, 2000]. Ross et al. (J Nutr 136:852S-854S, 2006) have, moreover, determined that allyl sulfur compounds derived from garlic modulate aberrant crypt foci (ACF) formation, structures which are considered to be early preneoplastic lesions of adenoma-carcinoma in humans and chemically induced colon cancer in rodents. Sumiyoshi et al. (Cancer Res 50:5084-5087, 1990) also demonstrated that certain organosulfur compounds found in garlic and onions can inhibit chemically induced colon cancer in mice. Reviews of the evidence pertaining to the ability of garlic and related allyl sulfur compounds to block tumors in the colon, lung, breast, and liver are presented in Milner (J Nutr 136:827S-831S, 2006); Aggarwal et al. (Biochemical Pharmacology 71:1397-1421, 2006); Cooper et al. (Biochemical Pharmacology 69:209-220, 2005); Khanum et al. (Critical Reviews in Food Science and Nutrition 44:479-488, 2004); Dorai et al. (Cancer Letters 215:129-140, 2004); Aggarwal et al. (Ann NY Acad Sci 1030:434-441, 2004); Borek et al. (J Nutr 131:1010S-10115S, 2001); and Kelloff et al. (J Cellular Biochem 26S:1-28, 1996). It is noteworthy that Milner, for example, emphasizes that additional studies are needed, with more modest exposure to allyl sulfur compounds over prolonged periods, in order to to establish this class of compounds as viable anticancer agents for humans. Milner also underscores that it is likely that variations in a variety of genetic and environmental factors may influence individual responses to allyl sulfur compounds.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A. Terminology

As used herein, the term "immunomodulator" refers to an agent which is able to modulate an immune response. An example of such modulation is an enhancement of cell activation or of antibody production.

An "immunological response" to a composition comprised of an antigen is the development in the host of a cellular- and/or antibody-mediated immune response to the composition of interest. Usually, such a response consists of the subject producing antibodies, B cells, helper T cells, suppressor T cells, and/or cytotoxic T cells directed specifically to an antigen or antigens included in the composition of interest.

The term "comprise" is generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention referred to above, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which specific binding members of the invention, or nucleic acid encoding such binding members will be, in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtiter plates for use in immunoassays, or will be mixed with pharmaceutically acceptable carriers or diluents when used in diagnosis or therapy.

As used herein, "pg" means picogram, "ng" means nanogram, "ug" or "μg" mean microgram, "mg" means milligram, "ul" or "μl" mean microliter, "ml" means milliliter, "l" or "L" means liter.

The term 'assay' means any process used to measure a specific property of a compound or agent. A 'screening assay' means a process used to characterize or select compounds based upon their activity from a collection of compounds.

"Preventing" or "prevention" refers to a reduction in risk of acquiring a disease or disorder.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

The term 'treating' or 'treatment' of any disease or infection refers, in one embodiment, to ameliorating the disease or infection (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease.

The phrase "pharmaceutically acceptable" refers to molecular entities and compositions that are physiologically tolerable and do not typically produce an allergic or similar untoward reaction, such as gastric upset, dizziness and the like, when administered to a human.

As used herein, the term "asymptomatic" refers to a condition or disease wherein the patient experiences no detectable symptoms. As described herein, MGUS and SMM are examples of asymptomatic myeloproliferative disorders.

The term "symptomatic" refers to a condition or disease wherein the patient experiences detectable symptoms of the condition or disease. As described herein, MM is an example of a symptomatic myeloproliferative disorder. Symptoms of MM include: fatigue, pale skin, and/or a fast or irregular heartbeat, which symptoms are associated with anemia; severe bone pain; increased risk of infection; nauseau and vomiting; loss of appetite, and/or excessive thirst, which symptoms are associated with hypercalcaemia; and a reduction of urine production and/or swelling in the legs and feet, which symptoms are associated with renal failure.

As used herein the term "nutraceutical" is used to refer to foods to which are added a substance to promote health.

B. Further Aspects of the Detailed Description

Assays for screening to identify agents, compounds, or peptides that target ER stress related signaling pathways are described herein. Agents, compounds, and peptides identified using screening methods described herein target cells with expansive, well-developed rough ERs, such as plasma cells, which are essentially factories dedicated to the constant synthesis and secretion of large amounts of immunoglobulin. By targeting ER stress related signaling pathways, such agents, compounds, and peptides can trigger cell death in target cells with expansive, well-developed rough ERs by inducing, for example, apoptosis.

In a further aspect, methods for treating asymptomatic myeloproliferative disorders, such as MGUS or SMM, comprising administering SAC, or a compound comprising SAC, or a composition comprising either of which to a subject afflicted with the asymptomatic myeloproliferative disorder are envisioned. Also encompassed herein is SAC, or a compound comprising SAC, or a composition comprising either of which for use in treating asymptomatic myeloproliferative disorders, such as MGUS or SMM and/or for use in the preparation of a medicament for the treatment of same.

In a still further aspect, methods for treating symptomatic myeloproliferative disorders, such as MM, comprising administering SAC, or a compound comprising SAC, or a composition comprising either of which to a subject afflicted with the symptomatic myeloproliferative disorder are envisioned. Also encompassed herein is SAC, or a compound comprising SAC, or a composition comprising either of which for use in treating a symptomatic myeloproliferative disorder, such as MM, and/or for use in the preparation of a medicament for the treatment of same. As described herein, SAC and compounds and compositions comprising same are envisioned for use in the treatment of MM either as the sole therapeutic agent or in conjunction with other therapeutic agents used to treat MM, such as BTZ.

Accordingly, SAC, compounds comprising SAC, and compositions comprising either of which have application and use, alone or in combination with other immune system modulators, T cell modulators, antibodies, vaccines, antigens, or chemotherapeutics for stimulating, facilitating or enhancing desired immune system or immune cell actions or activities, particularly those directed against asymptomatic and/or symptomatic myeloproliferative disorders, that result in a reduction in plasma cell load and/or improved patient survival.

Agents, compounds, and compositions of the present invention may be administered to a patient in need of treatment via any suitable route, including by intravenous, intraperitoneal, intramuscular injection, or orally. The precise dose will depend upon a number of factors, including whether the agents, compounds, or compositions are for treatment or for prevention. The dosage or dosing regime of an adult patient may be proportionally adjusted for children and infants, and also adjusted for other administration or other formats, in proportion for example to molecular weight or immune response. Administration or treatments may be repeated at appropriate intervals, at the discretion of the physician.

Agents and compounds described herein are generally administered in the form of a pharmaceutical composition, which may comprise at least one component in addition to the agents and compounds. Pharmaceutical compositions according to the present invention, and for use in accordance with the present invention, may comprise, in addition to active ingredient, a pharmaceutically acceptable excipient, carrier, buffer, stabiliser or other materials known to those skilled in the art. Such materials should be non-toxic and should not interfere with the efficacy of the active ingredient. The precise nature of the carrier or other material will depend on the route of administration, which may be oral, or by injection, e.g. intravenous, or by deposition at a tumor site.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

Exemplary pharmaceutical compositions for oral administration are disclosed in, for example, U.S. Pat. No. 8,217,084 and US Patent Application Publication No. US 2004/0170707, the entire of content of each of which is incorporated herein by reference. US 2004/0170707, for example, discloses garlic supplements that comprise a core of garlic encapsulated by an enteric coating and a deodorizing layer.

Aged Garlic Extract (AGE), which is produced by the Wakugana Corporation (worldwide web kyolic.com) is another product envisioned for use in the present method. AGE comprises primarily the water-soluble compounds S-allylcysteine (SAC, 0.62 mg/g) and SAMC (0.14 mg/g), but also comprises the lipid-soluble compounds diallyl sulfide, triallyl sulfide, and DiAllylDisulfide (DADS, AllylSSAllyl or ASSA). In light of the above, AGE predominantly consists of SAC. Additional compositional information pertaining to AGE is as follows: it contains no allicin and the total amount of sulfur compounds is 2.14 mg/g. See, for example, U.S. Pat. No. 8,217,084 and references cited therein, the entire content of each of which is incorporated herein by reference.

As described by Sumiyoshi et al. (Nihon Yakurigaku Zasshi 110 Suppl:93P-97P, 1997), the anti-carcinogenic activities of garlic and its constituents have been demonstrated using several animal models, but none that relate to myeloproliferative disorders. Garlic preparations have been also shown to lower serum cholesterol and triglyceride levels through inhibition of their bio-synthesis in the liver and to inhibit oxidation of low density lipoprotein. These findings have suggested the use of garlic preparations in the treatment of cardiovascular diseases, wherein elevated serum cholesterol and triglyceride levels are significant risk factors. In vitro and in vivo studies have, furthermore, revealed that aged garlic extract stimulates immune functions, such as proliferation of lymphocytes, cytokine release, NK activity and phagocytosis.

Further to the above, Borek et al. [The Journal of Nutrition 131 (Supp 35):1010S, 2001; the entire content of which is incorporated herein by reference], have shown that AGE has been shown to exhibit antioxidant activity. The antioxidant activity described by Borek et al. prevents the cellular damage and deleterious effects of reactive oxygen species. In contrast, in the system described herein, SAC appears to be initiating signaling cascades to induce ER stress and cause apoptosis and, although not wishing to be bound by theory, SAC may be acting via reactive oxygen species messengers. That being the case, the present inventors propose using SAC to promote cellular death in a target population of cells already experiencing ER stress related conditions, which is quite the opposite of the disclosure of Borek et al., which suggests that SAC can act to preserve cellular integrity.

SAC can be purchased from a variety of companies, including LKT Laboratories, Inc. (St. Paul, Minn.) and Wakunaga Pharmaceutical (Osaka, Japan). SAC suitable for laboratory purposes can also be purchased from Sigma.

For intravenous injection, or injection at the site of affliction, the active ingredient may be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

A composition may be administered alone or in combination with other treatments, therapeutics or agents, either simultaneously or sequentially, dependent upon the condition to be treated. In addition, the present invention contemplates and includes compositions comprising the agents and compounds herein described and other agents or therapeutics such as immune modulators, antibodies, immune cell stimulators, or adjuvants. In addition, the composition may be administered with hormones, such as dexamethasone, immune modulators, such as interleukins, tumor necrosis factor (TNF) or other growth factors, colony stimulating factors, or cytokines which stimulate the immune response. The composition may also be administered with, or may include combinations along with immune cell antigen antibodies or immune cell modulators.

The preparation of therapeutic compositions which contain agents or compounds as active ingredients is well understood in the art. Typically, such compositions are prepared as injectables, either as liquid solutions or suspensions. However, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

Agents or compounds can be formulated into a therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The agent or compound containing compositions are conventionally administered intramuscularly, intravenously, as by injection of a unit dose, or orally, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of activation and immune response desired. Precise amounts of active ingredient required to be administered depend on the judgment of the practitioner and are peculiar to each individual. Suitable regimens for initial administration and follow on administration are also variable, and may include an initial administration followed by repeated doses at appropriate intervals by a subsequent injection or other administration.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

Compositions and dosing parameters relating to use of various garlic products, including blended fresh garlic and garlic supplements, in a clinical trial relating to reducing serum lipid levels are described by Lawson et al. (J Agric Food Chem 53(16)6254-6261, 2005; the entire content of which is incorporated herein by reference). Garlic supplements described in detail therein include: Garlicin® (Nature's Way Products, Inc., Springville, Utah 84663, USA) and Kyolic® Hi-Po Formula 100 (Kyolic) (Wakunaga of America Co., Ltd., Mission Viejo, Calif. 92691, USA). Additional garlic supplements are known in the art and described in, for example, Borek et al. (J Nutr 131:1010S-1015S, 2001). Dosing parameters may also be determined based on the disclosure of Rosen et al. (Biofactors 13(1-4): 241-249, 2000; the entire content of which is incorporated herein by reference).

With regard to Kyolic Reserve Garlic, for example, dosing parameters may be based on 600 mg/day as a preventive dose and up to 5400 mg/day as a cancer adjuvant in combination with a chemotherapeutic agent, such as, for example, dooxorubicin. See, for example, the LifeExtension website. Additional studies pertaining to the antiatherosclerotic properties of garlic suggest a dose of 600 mg of a commercial garlic powder powder (tablet) once per day for 2 weeks (Phelps et al. Lipids 28:475-477, 1993); 7.2 g AGE per day for 3 months (Steiner et al. J Cardiovasc Pharmacol 31:904-908, 1998); or 1.2 g AGE, three times per day for 2 weeks (Lau et al. J Nutr 131:9855-9885, 2001).

Based on the findings presented herein and the disclosures indicated hereinabove, dosing regimens of 500-2,500 mg of AGE per day are envisioned to be effective for the treatment of MGUS, SMM, and/or MM. Such a dosing range is thought to be effective for restoration and/or maintainance of normal serum plasma concentrations in subjects afflicted with MGUS, SMM, or MM. In a particular dosing regimen, three doses of 500 mg tablets of AGE per day are envisioned to be sufficient to restore/maintain normal serum plasma concentration effective for the treatment of MGUS, SMM, and/or MM.

Therapeutic and/or Preventative Efficacy

The therapeutic and/or preventative efficacy of the methods and agents described herein may be assayed using a variety of techniques and approaches, such as those described by Golombick et al. (Am J Hematol. 87:455-460, 2012), the entire content of which is incorporated herein by reference. In brief, blood and urine samples can be isolated and analyzed before the onset of methods described herein, so as to establish a baseline reading for a patient, and at various stages during treatment, so as to assess efficacy in an ongoing fashion during treatment. Blood and urine samples can also be isolated from a patient after methods described herein have been completed and and the samples analyzed for the purposes of establishing whether durable effects of the treatment/preventative measures are apparent or if clinical indicators return and the time frame in which they reappear. Serum paraprotein and immunoglobulin-electrophoresis may, for example, be quantitated by agarose gel.

Efficacy of the preventative and/or therapeutic methods described herein can be assessed by assaying a number of clinical indicators of disease, including: measuring the free light-chain ratio (rFLC) and the difference between clonal and nonclonal light-chain (dFLC) and involved free light-chain (iFLC), wherein a reduction in any of these parameters is a positive indicator of efficacy. A decrease in urinary deoxypyridinoline (uDPYD), a marker of bone resorption is also an indicator of efficacy, as is a decrease in serum creatinine levels. Total serum protein, random urinary protein concentration, and serum paraprotein concentration can also be assessed as clinical indicators of disease.

FLC analysis may be performed by immunonephelometry using specific antibodies (the binding site) on, for example, a BNI nephelometer (Dade Behring, Deerfield, Ill.). See, for example, Golombick et al. (Am J Hematol. 87:455-460, 2012) for additional methodological details. The FLC assay independently measures free kappa light chains, wherein the normal range is 3.3-19.4 mg/L, and free lambda light chains, wherein the normal range is 5.7-26.3 mg/L. On the basis of the ratio of kappa to lambda light chain levels (normal reference range, 0.26-1.65), the assay also facilitates an analysis clonality. Patients with a kappa/lambda FLC ratio <0.26 are generally defined as having monoclonal lambda FLC and those with a ratio of >1.65 are defined as having monoclonal kappa FLC. If a patient's FLC ratio is >1.65, kappa light chain is designated the "involved" FLC and lambda is designated the "uninvolved" light chain for that patient. In contrast, if a patient's FLC ratio is <0.26, lambda light chain is designated the "involved" FLC and kappa is designated the "uninvolved" light chain for that patient.

uDPYD, which is a marker of bone resorption, may be measured using a chemiluminescence immunometric assay (Diagnostic Products, Los Angeles, CA; % coefficient of variation (CV)=15% at 30 nmol/L and 10% at 100 nmol/L). See also Golombick et al. (supra).

The serum FLC assay is an extremely sensitive assay that accurately quantitates the concentration of free kappa and lambda light chains, which are those light chains not bound by to intact Ig. An abnormal kappa/lambda FLC ratio reflects an excess of one or another of the light chains relative to the other and is viewed as a surrogate of clonal expansion in MGUS and SMM. An abnormal FLC ratio is, moreover, viewed as indicative of a high risk of progression to MM (Rajkumar et al. Blood 106:812-817, 2005). Serial monitoring of serum FLC is also considered an accurate indicator of tumor cell kill (Siegel et al. Labmedicine 40:363-387, 2009). Serial changes in the iFLC or dFLC are also disclosed as potentially better indicators of treatment response than the FLC ratio (Siegel et al., supra).

EXAMPLE 1

The present study identified SAC as a potent inhibitor of myeloma proteostasis as demonstrated by its ability to inhibit secretion of Gaussia luciferase (Glue), a naturally secreted luciferase that can be easily monitored in transfected cells through extracellular release of luciferase activity in real time [Badr et al. *PLoS One* 2, e571, 2007]. For screening, KMS11 and ARP1 cells were seeded in 96-well plates and treated with 5 µM of compounds from the Spectrum library (Microsource Discoveries) for 24 hours. Conditioned medium from each compound treatment was harvested to assay Gluc secretion alongside samples treated with DMSO alone, BTZ and TM as controls. Compounds of interest were considered to be those that inhibit Gluc secretion in both cell lines by at least 30% after 24 hours treatment. As shown in FIG. 1, 5 µM SAC inhibited Gluc secretion as effectively as 5 µM BTZ. For these studies, 10 µg/ml tunicamycin (TM) and 5 µM BTZ were used as positive controls since they are known to disrupt proteostasis. These controls also serve as a proof of principle that the screening system can effectively identify agents that promote ER stress and may serve as potential therapeutic agents for MGUS and MM and as preventative agents that delay or inhibit progression to MM. Additionally, the well characterized DNA damaging agent cisplatin (CIS) was used as a negative control since it does not induce ER stress. It is believed that the ability of SAC to disrupt cellular proteostasis has not been described previously.

Figure 2:
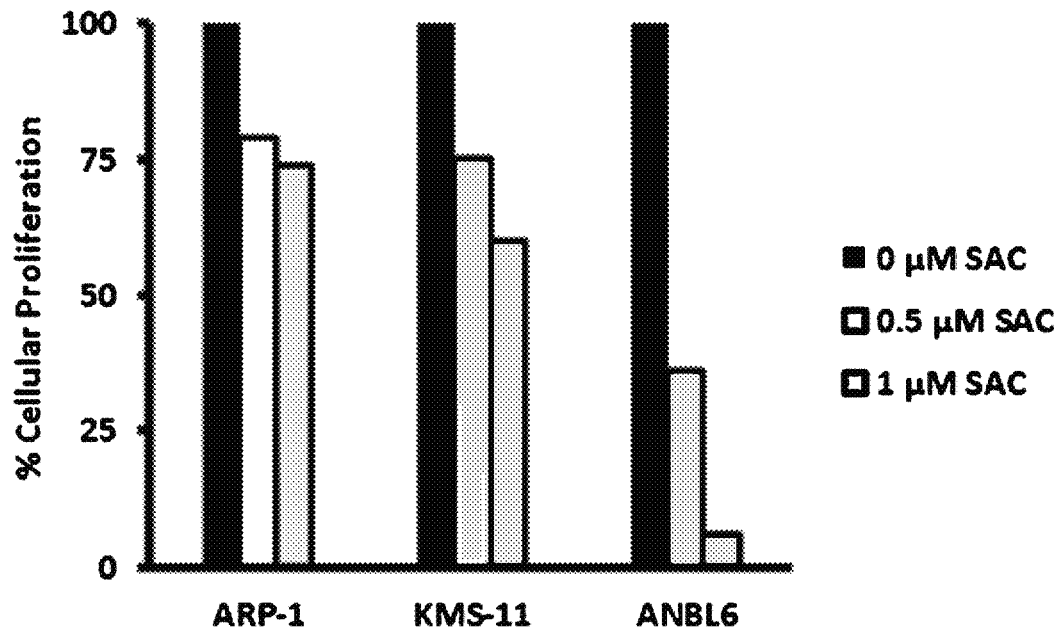
FIG. 2 shows that SAC inhibits cellular proliferation in KMS11 and ARP1 cells. Cellular proliferation was assessed after 72 hour treatment by MTT assay and expressed as a percentage relative to vehicle control.

In addition to disrupting proteostasis, SAC also inhibits proliferation of multiple myeloma cells as shown in FIG. 2. Further to the above, it is thought that the present findings are the first to demonstrate that SAC possesses antiproliferative activity with respect to multiple myeloma cells.

The present inventors have also investigated the effect of SAC on protein folding in MM cells. Protein folding is a complex process that requires chaperone proteins, glycosylating enzymes, and the proper oxidizing environment. ER stressors impair this process and cause accumulation of unfolded or misfolded proteins, leading to activation of the unfolded protein response (UPR) comprised of 3 pathways. Activation of IRE1 (inositol-requiring protein-1) by ER stress signaling causes sequence specific cleavage and subsequent splicing of mRNA encoding the transcription factor XBP1. XBP1s, the spliced form of XBP1, induces expression of the majority of UPR related genes (Tabas et al. Nat Cell Biol, 2011. 13(3):184-90; the entire content of which is incorporated herein by reference).

In order to elucidate further the mechanism of SAC-mediated ER stress responses, the present inventors evaluated the key UPR marker cleaved XBP1 (Calfon et al. Nature, 2002. 415(6867): 92-6; Doudican et al. Oncol Rep, 2012. 28(5):1851-8). As shown in FIG. 6, activation of the IRE1 arm of the UPR response was observed through enhanced splicing of the UPR transcription factor XBP1 upon treatment with SAC in both KMS11 and ARP1 multiple myeloma cells. The level of spliced XBP1 observed upon treatment with SAC is similar to cells treated with the positive control tunicamycin (TM). The present inventors have, therefore, demonstrated that SAC induces ER stress in multiple myeloma cells as evidenced by XBP1 cleavage and these findings suggest that SAC would confer therapeutic benefit to a subject afflicted with MM via inducing ER stress in MM cells in the subject. Further to this point, administration of SAC to subjects with MGUS or SMM would also induce ER in aberrant MGUS and SMM cells in the subjects.

To explore the effects of SAC in the context of SMM, the present inventors tested the activity of SAC in bone marrow (BM) mononuclear cells isolated from a patient with smoldering multiple myeloma (SMM). To isolate the BM mononuclear cells, heparinized BM samples were freshly obtained from a SMM patient, diluted in PBS, and subjected to Ficoll-Hypaque density separation. Mononuclear cells are carefully collected from the PBS-Ficoll interface, washed in PBS and pelleted. The cell proliferation assay was performed by seeding the SMM BM mononuclear cells in 96-well plates at a density of 5000 cells per well. After overnight incubation, cells were treated with SAC at concentrations ranging from 100 nM to 10000 nM. After a 72 hr incubation period, proliferation was assessed using a tetrazolium dye reduction assay (CellTiter 96 AQueous Non-Radioactive Cell Proliferation Assay; Promega, Madison, Wis.). Absorbance was recorded on a microplate reader at 490 nm. Cellular proliferation was expressed as a percentage with vehicle-treated cells set at 100%. Each assay was performed in triplicate with mean values reported.

Figure 7:
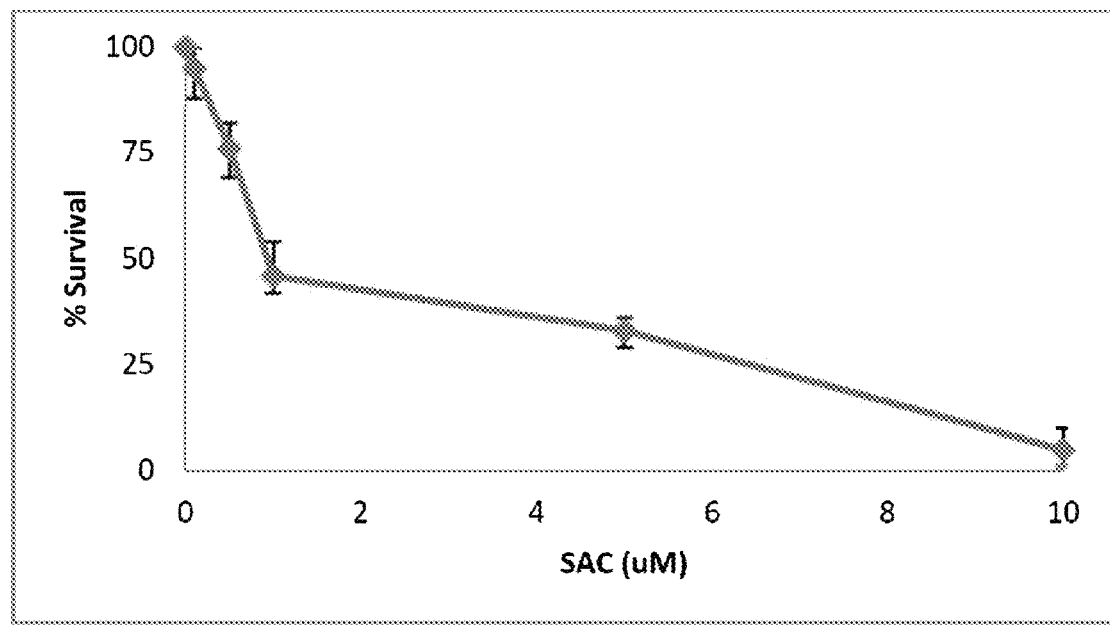
FIG. 7 shows that SAC inhibits cellular proliferation in bone marrow (BM) mononuclear cells isolated from a human subject with SMM. Cellular proliferation was assessed after 72 hour treatment by MTT assay and expressed as a percentage relative to vehicle control.

The results of this assay are depicted in FIG. 7, which shows that treatment of SMM BM mononuclear cells with SAC results in dose-dependent inhibition of cellular proliferation. These findings affirm the usefulness of SAC in the context of treating SMM and MGUS and promote the administration of SAC as a prophylatic treatment to inhibit the progression of SMM to frank MM.

While certain of the particular embodiments of the present invention have been described and specifically exemplified herein, it is not intended that the invention be limited to such embodiments. Various modifications may be made thereto without departing from the scope and spirit of the present invention, as set forth in the following claims.

What is claimed is:

1. A method for treating a myeloproliferative disorder in a subject, wherein the myeloproliferative disorder is monoclonal gammopathy of undetermined significance (MGUS), smoldering myeloma (SMM), or multiple myeloma (MM), the method comprising administering a therapeutically effective amount of S-allylcysteine (SAC) or a composition thereof to the subject.

2. The method of claim 1, wherein the subject has treatment resistant MM.

3. The method of claim 1, further comprising a chemotherapeutic agent.

4. The method of claim 3, wherein the chemotherapeutic agent is bortezomib (BTZ).

5. The method of claim 1, wherein the subject is in remission following treatment for MM.

6. The method of claim 1, wherein the composition consists essentially of SAC or consists of SAC.

7. A method for treating a myeloproliferative disorder characterized by monoclonal plasma cell proliferation in a subject, the method comprising providing the subject afflicted with an asymptomatic myeloproliferative disorder, wherein the asymptomatic myeloproliferative disorder is monoclonal gammopathy of undetermined significance (MGUS) or smoldering myeloma (SMM), and administering a therapeutically effective amount of S-allylcysteine (SAC) or a composition thereof to the subject to target cells involved in the disorder for cell killing via ER stress mediated pathways and thereby treat the myeloproliferative disorder.

8. A method for treating a myeloproliferative disorder characterized by monoclonal plasma cell proliferation in a subject, the method comprising providing a subject afflicted with a symptomatic myeloproliferative disorder, wherein the symptomatic myeloproliferative disorder is multiple myeloma (MM), and administering a therapeutically effective amount of S-allylcysteine (SAC) or a composition thereof to the subject to target cells involved in the disorder for cell killing via ER stress mediated pathways and thereby treat the myeloproliferative disorder.

9. The method of claim 8, wherein the subject has treatment resistant MM.

10. The method of claim 8, further comprising a chemotherapeutic agent.

11. The method of claim 10, wherein the chemotherapeutic agent is bortezomib (BTZ).

12. The method of claim 8, wherein the subject is in remission following treatment for MM.

13. The method of claim 1, wherein the subject is a mammal.

14. The method of claim 13, wherein the mammal is a human.

15. The method of claim 7, wherein the subject is a mammal.

16. The method of claim 15, wherein the mammal is a human.

17. The method of claim 8, wherein the subject is a mammal.

18. The method of claim 17, wherein the mammal is a human.

* * * * *